United States Patent
Doll et al.

(10) Patent No.: US 10,022,184 B2
(45) Date of Patent: Jul. 17, 2018

(54) MEDICAL INSTRUMENT AND ELECTROSURGICAL SYSTEM

(71) Applicant: Karl Storz SE & Co. KG, Tuttlingen (DE)

(72) Inventors: Frank Doll, Talheim (DE); Martin Hahn, Leibertingen-Altheim (DE); Uwe Wittke, Tuttlingen-Moehringen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 536 days.

(21) Appl. No.: 14/471,749

(22) Filed: Aug. 28, 2014

(65) Prior Publication Data

US 2015/0066018 A1 Mar. 5, 2015

(30) Foreign Application Priority Data

Aug. 30, 2013 (DE) .......................... 10 2013 109505

(51) Int. Cl.
*A61B 18/16* (2006.01)
*A61B 18/14* (2006.01)
*A61B 18/12* (2006.01)
*A61B 18/00* (2006.01)

(52) U.S. Cl.
CPC .......... *A61B 18/16* (2013.01); *A61B 18/1206* (2013.01); *A61B 18/149* (2013.01); *A61B 18/1492* (2013.01); *A61B 2018/00601* (2013.01); *A61B 2018/126* (2013.01); *A61B 2018/144* (2013.01); *A61B 2018/1405* (2013.01); *A61B 2018/1475* (2013.01); *A61B 2018/162* (2013.01)

(58) Field of Classification Search
CPC .............. A61B 18/1206; A61B 18/149; A61B 18/1492; A61B 18/16; A61B 2018/00601; A61B 2018/126; A61B 2018/1405; A61B 2018/144; A61B 2018/1475; A61B 2018/162
USPC .......................................................... 606/48
See application file for complete search history.

(56) References Cited

U.S. PATENT DOCUMENTS

| | | |
|---|---|---|
| 4,116,198 A | 9/1978 | Roos |
| 5,196,011 A | 3/1993 | Korth et al. |
| 6,471,701 B2 | 10/2002 | Brommersma et al. |

(Continued)

FOREIGN PATENT DOCUMENTS

| | | |
|---|---|---|
| DE | 2521719 A1 | 11/1976 |
| DE | 4032601 A1 | 4/1992 |

(Continued)

*Primary Examiner* — Joseph Stoklosa
*Assistant Examiner* — Tigist Demie
(74) *Attorney, Agent, or Firm* — Whitmyer IP Group LLC

(57) ABSTRACT

Bipolar medical instrument for cutting tissue under the action of high-frequency current, wherein the instrument extends along a longitudinal direction from a proximal end to a distal end, wherein an active electrode and a neutral electrode, adjacent to the active electrode, are arranged at the distal end, and wherein the neutral electrode has a curved profile with a first curvature and a second curvature, wherein the respective directions of the curvatures are different. An electrosurgical system is also disclosed, with a high-frequency generator, and with one such bipolar medical instrument, which can be attached to the high-frequency generator.

19 Claims, 6 Drawing Sheets

(56) References Cited

U.S. PATENT DOCUMENTS

| | | | | |
|---|---|---|---|---|
| 6,494,881 | B1* | 12/2002 | Bales | A61B 18/149 |
| | | | | 606/41 |
| 6,730,081 | B1* | 5/2004 | Desai | A61B 17/00234 |
| | | | | 604/8 |
| 7,611,511 | B2 | 11/2009 | Blocher | |
| 2004/0002702 | A1 | 1/2004 | Xiao et al. | |
| 2005/0245927 | A1 | 11/2005 | Snay et al. | |
| 2005/0251134 | A1* | 11/2005 | Woloszko | A61B 18/149 |
| | | | | 606/46 |
| 2012/0150179 | A1* | 6/2012 | Feinberg | A61B 18/1445 |
| | | | | 606/48 |
| 2012/0310233 | A1* | 12/2012 | Dimmer | A61B 18/1492 |
| | | | | 606/33 |

FOREIGN PATENT DOCUMENTS

| | | |
|---|---|---|
| EP | 1163886 A2 | 12/2001 |
| EP | 1567079 B1 | 8/2006 |
| WO | 9916371 A1 | 4/1999 |

\* cited by examiner

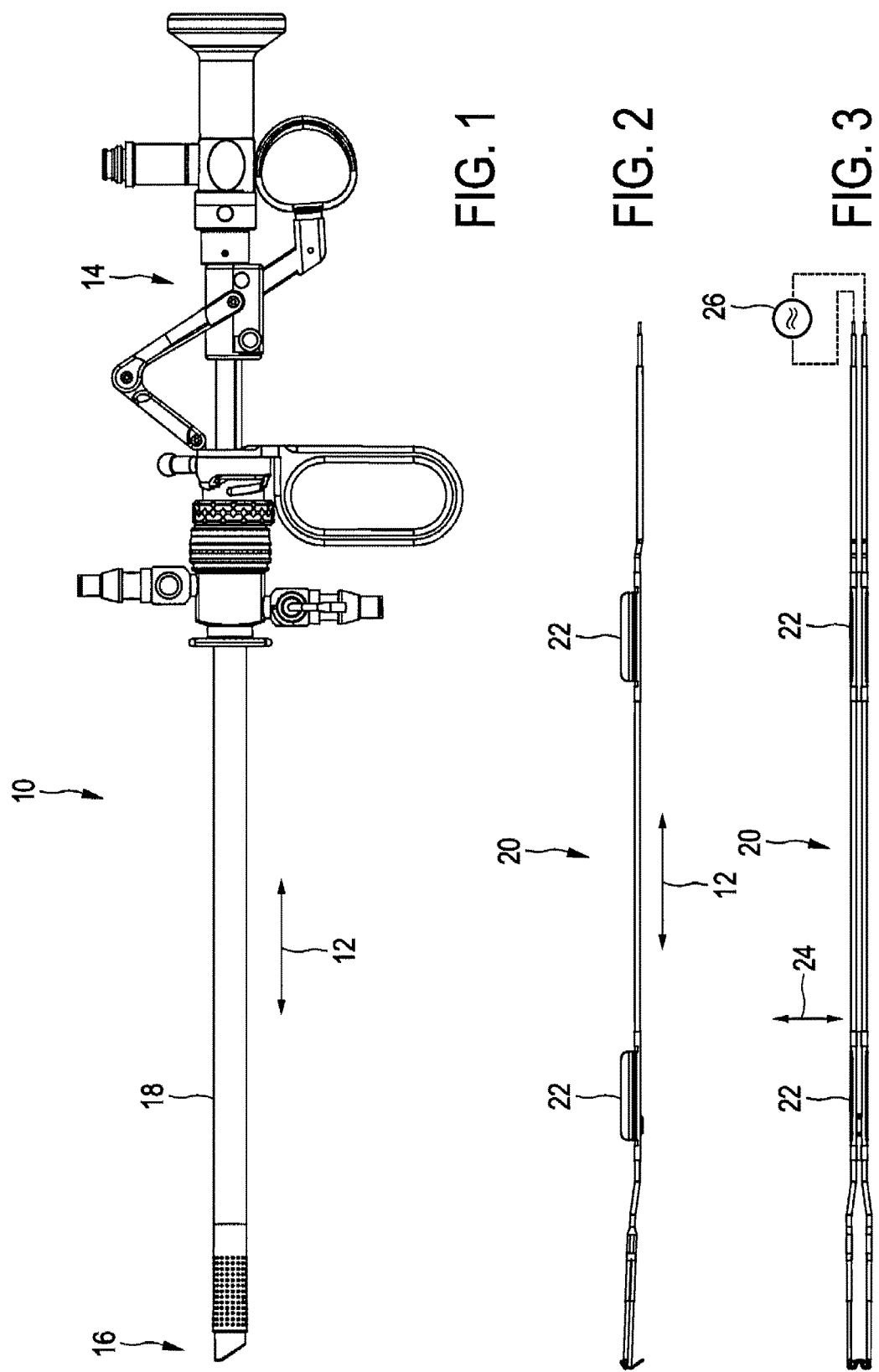

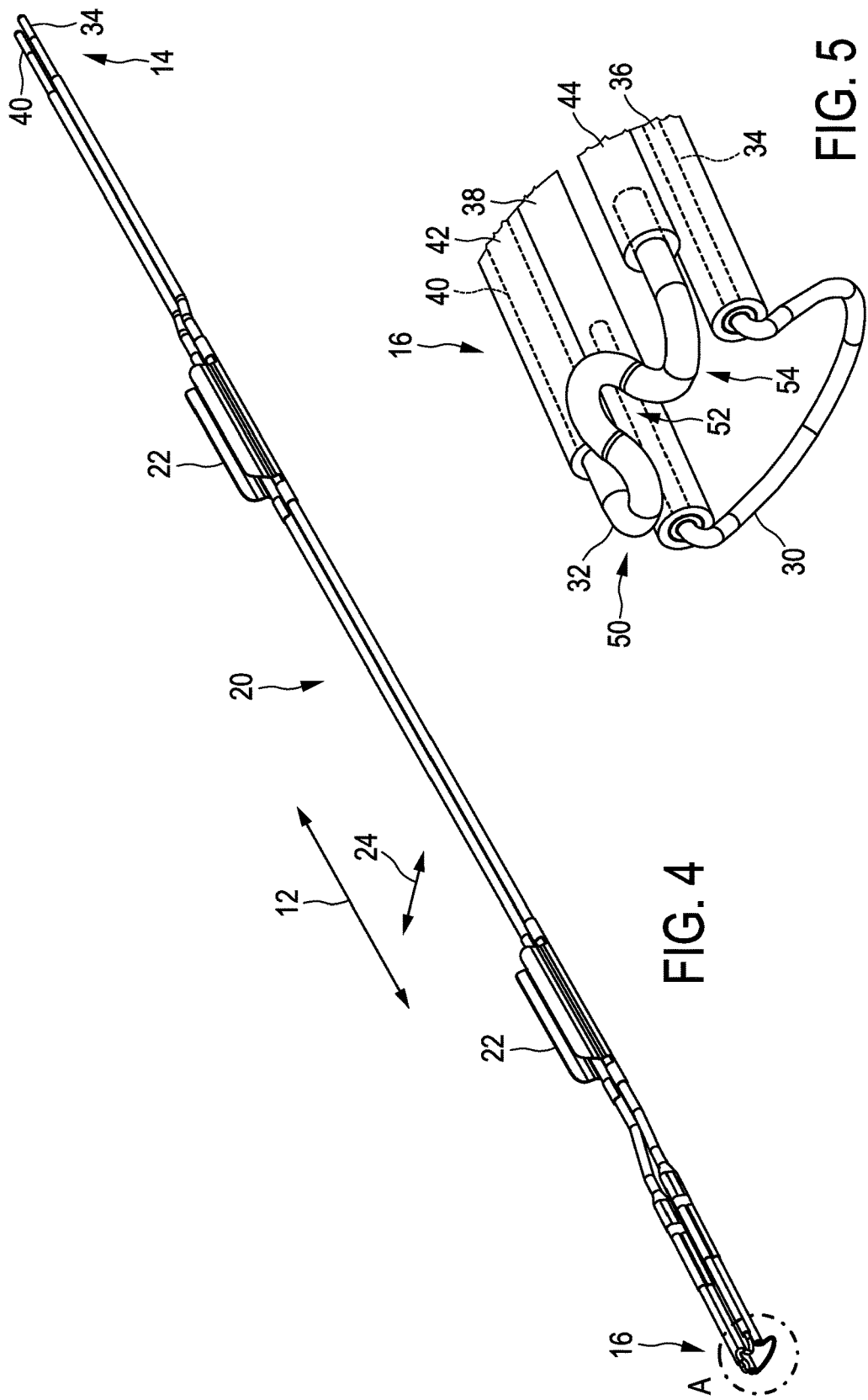

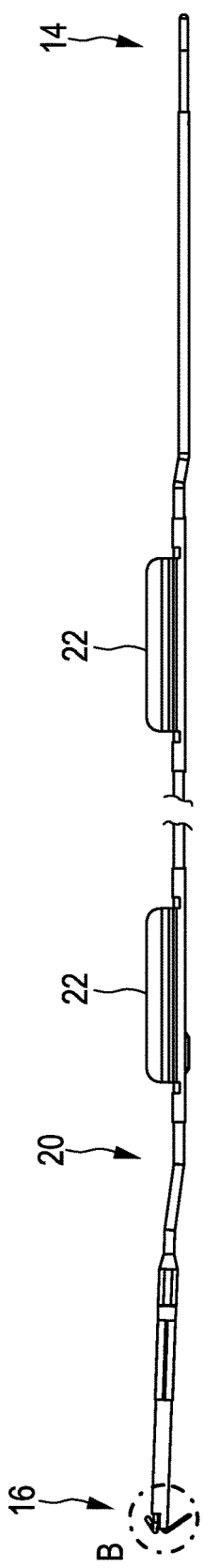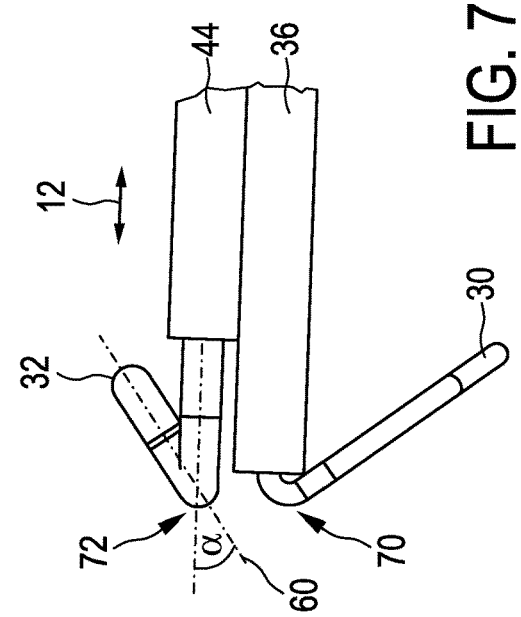

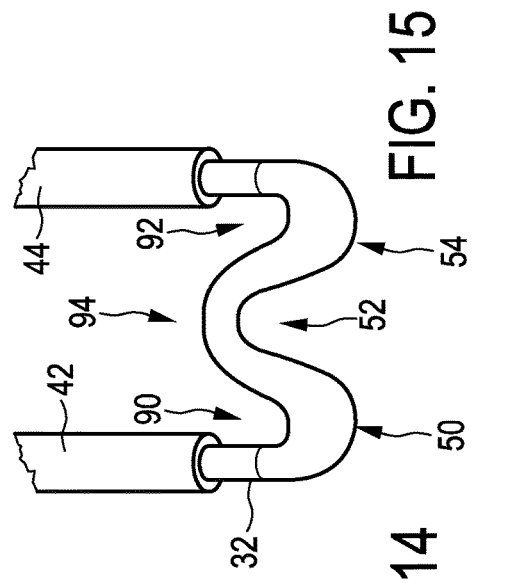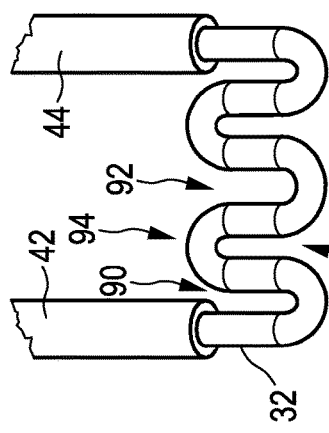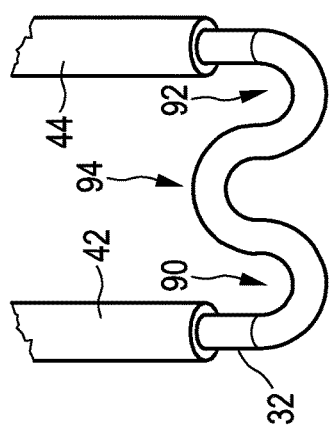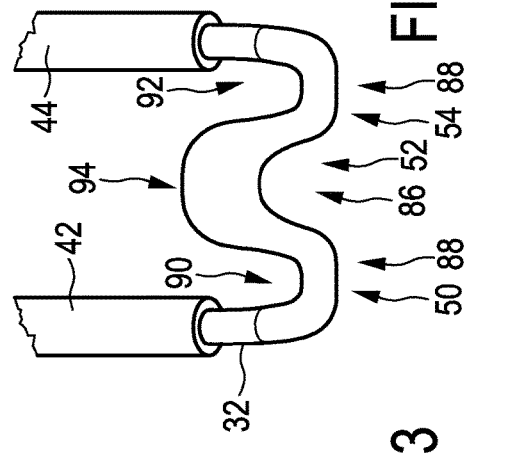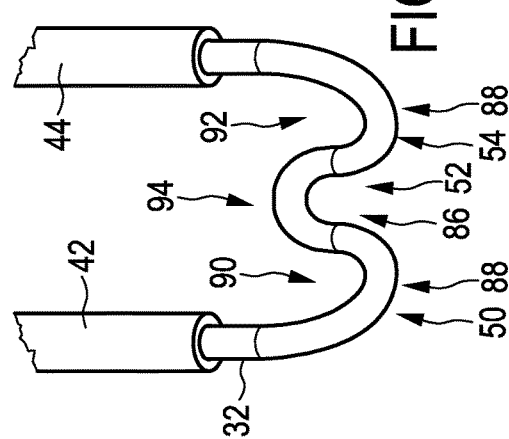

MEDICAL INSTRUMENT AND ELECTROSURGICAL SYSTEM

CROSSREFERENCES TO RELATED APPLICATIONS

This application claims priority from German patent application DE 10 2013 109 505.4, filed on Aug. 30, 2013. The entire content of this priority application is incorporated herein by reference.

BACKGROUND

A bipolar medical instrument is disclosed for cutting tissue under the action of high-frequency current, wherein the instrument extends along a longitudinal direction from a proximal end to a distal end, and wherein an active electrode and a neutral electrode, adjacent to the active electrode, are arranged at the distal end. There is also disclosed an electrosurgical system with a high-frequency generator and with an instrument of the type indicated above.

An instrument and a system of the type indicated above is shown in DE 25 21 719.

An instrument and a system of the type indicated above are used in open surgery, but preferably in minimally invasive surgery, for cutting tissue in the human or animal body.

In the context of the present disclosure, the instrument indicated above, when used in minimally invasive surgery, can be combined with an endoscope to form what is known as a resectoscope, or it can itself constitute such a resectoscope.

Electrosurgery, or high-frequency surgery, is employed therapeutically in various medical specialties, for example in urology, gynecology, neurosurgery, abdominal surgery, etc. In urology in particular, prostate tissue is removed endoscopically in minimally invasive surgery by means of an instrument of the type indicated above.

In electrosurgical resectoscopy techniques, a distinction is made between monopolar and bipolar application of high-frequency current.

In monopolar application, only the active electrode, sometimes also referred to as the cutting electrode or treatment electrode, is introduced into the treatment region, while the neutral electrode is arranged externally on the patient. Consequently, the current flow between the active electrode and the neutral electrode passes through the patient's body, the disadvantage being that the current path through the patient cannot be safely controlled, the result of which is the possibility of damage to the organs. In addition, the neutral electrode placed on the patient's body may cause burning of the patient's skin.

In the bipolar technique, to which the present disclosure relates, the active electrode and the neutral electrode are both introduced into the treatment region. The current flow can in this way be limited in a controllable manner to the area between the active electrode and the neutral electrode, such that it flows spatially only between the active electrode and the neutral electrode. Accordingly, medical instruments of the type indicated at the outset have been created in which the active electrode and the neutral electrode are arranged on an electrode carrier, in such a way that the active electrode and the neutral electrode can be introduced adjacent to each other into the treatment region.

In bipolar medical instruments of the type indicated at the outset, the active electrode is usually configured with a small active surface area so that a high current density is created on the active electrode, whereas the neutral electrode is usually configured with a relatively large surface area so that only moderate or low current densities are created on the neutral electrode. The active electrode is accordingly used for cutting, while the neutral electrode is intended as far as possible to have no effect on the tissue and is intended simply to limit the current path to the area between the active electrode and the neutral electrode.

In the instrument known from the abovementioned document DE 25 21 719, the neutral electrode is configured as a broad tape, while the active electrode is configured as a wire loop. In a further illustrative embodiment in DE 25 21 719, the neutral electrode, on its side facing away from the active electrode, is covered by a plastic extension, which is connected fixedly to the shaft of the resectoscope.

WO 99/16371 A1 likewise discloses a bipolar medical instrument of the type indicated at the outset. Similarly to the known instrument described above, the active electrode is positioned with respect to the neutral electrode, in the direction transverse to the longitudinal axis, such that they are not spaced apart from each other.

EP 1 163 886 A2 discloses a resectoscope instrument in which the active electrode and the neutral electrode are electrically separated on their mutually facing sides by an insulating body, such that each straight line of connection between the electrodes passes through the insulating body. This is intended to ensure that the direct current flow between the two electrodes is made difficult or is reduced.

The known instruments are either unsuitable for use in particularly small cavities, are too expensive to produce or do not offer sufficient protection for avoiding undesired perforation in the walls of the cavities.

SUMMARY

The object is to make available an improved instrument and an improved system of the type indicated at the outset.

According to a first aspect, a medical instrument of the type indicated at the outset is disclosed in which the neutral electrode has a curved profile with a first curvature and a second curvature, wherein the respective directions of the curvatures are different.

Such a shape can have the effect of being atraumatic, since the neutral electrode, at its distal limit, no longer has a straight edge, and instead has a curved profile at the distal end. While a straight edge poses some risk of the physician inadvertently cutting into tissue with the neutral electrode when using the instrument, this risk is reduced by the proposed design.

For better understanding, the curvatures should be considered, according to some exemplary embodiments, in a plane of projection spanned by the longitudinal direction and by a transverse direction perpendicular to the latter. The transverse direction should be understood, according to some exemplary embodiments, as having the direction of the straight connecting line between the two points at which the neutral electrode is held relative to the instrument. In FIG. 3 below, the plane of the drawing represents this stated plane of projection.

In an exemplary embodiment, the radii of the curvatures are the same size and, in another exemplary embodiment, they are chosen to be of different sizes. In certain exemplary embodiments, one, more or all of the curvatures have a constant radius, whereas, in other exemplary embodiments, one, more or all of the curvatures have a varying radius, wherein, according to some exemplary embodiments, a spiral-like shape can be formed. It is preferable if the active electrode is designed as a wire loop.

In an exemplary embodiment, the curved profile has at least three curvatures, and the directions of the curvatures change twice along the extension of the neutral electrode.

In this way, the neutral electrode may be made atraumatic. In certain embodiments, the neutral electrode has four or more curvatures. It is left to a person skilled in the art to make a suitable choice regarding the particular use and the maximum desired size of the neutral electrode. If the neutral electrode is to be made small, as is desirable in particular for urological measures, an exemplary embodiment with three curvatures may be chosen. In other exemplary embodiments, the curved profile has at least four curvatures, at least five curvatures or at least six curvatures.

In another exemplary embodiment, the neutral electrode is designed as a wire element.

This embodiment may be achieved rather easily from the point of view of production engineering. The wire can have a circumference composed of straight lines and/or arcs.

In another exemplary embodiment, a first surface of the active electrode is smaller than a second surface of the neutral electrode.

This embodiment means that, when contact is made with tissue, firing takes place as far as possible on the active electrode and not on the neutral electrode, even when the latter is undesirably touching tissue. It is preferable to obtain the larger second surface by the fact that at least an average cross section of the neutral electrode is larger than an average cross section of the active electrode and/or that the extent of the neutral electrode along its physical extension is greater than the extent of the active electrode.

In an exemplary embodiment, the extent of the neutral electrode along its physical extension is at least 5% greater according to some exemplary embodiments, at least 10% greater according to other exemplary embodiments, at least 20% greater according to yet other exemplary embodiments and at least 30% greater according to still other exemplary embodiments, than the extent of the active electrode along the physical extension of the latter.

In another exemplary embodiment, a cross-sectional profile of the neutral electrode has a rounded shape, and, according to some exemplary embodiments, an at least substantially oval or at least substantially circular shape.

This embodiment may offer benefits from the point of view of production engineering.

In another exemplary embodiment, the neutral electrode has a constant cross section, according to some exemplary embodiments, a constant diameter, along its physical extension.

This embodiment, too, may offer benefits in respect of production.

In another exemplary embodiment, the neutral electrode, in a plan view, has at least approximately a wave shape and, according to some exemplary embodiments, at least approximately a W shape.

Such an embodiment may offer an atraumatic use. In this connection, it is preferable if the W shape is generously rounded. In the context of this application, the term generously is to be understood as meaning that the radius of a curvature accounts for at least 4% according to some exemplary embodiments, at least 8% according to other exemplary embodiments, at least 11% according to yet other exemplary embodiments and at least 13% according to still other exemplary embodiments, of the extent of the neutral electrode in the transverse direction.

In another exemplary embodiment, the neutral electrode has at least two curved portions or, according to some exemplary embodiments, at least three curved portions, each of which, according to some exemplary embodiments, has at least approximately the shape of a partial oval or of a partial circle.

In such an embodiment, a good atraumatic effect is seen, especially if the radii of the curved portions are generously dimensioned.

In another exemplary embodiment, the active electrode and the neutral electrode are located, in a retracted state, inside a distal end of a shaft of the instrument.

This embodiment may allow the instrument to be introduced in an atraumatic manner into the cavity that is to be treated.

In relation to the longitudinal direction, a distal end of the active electrode in another exemplary embodiment is arranged further distally than a distal end of the neutral electrode or, in relation to the longitudinal direction, a distal end of the active electrode is arranged at the same distal extent as a distal end of the neutral electrode.

This embodiment helps ensure that the active electrode comes into contact with tissue first or comes into contact with tissue at least simultaneously with the neutral electrode. This in turn contributes to the firing taking place on the active electrode and not on the neutral electrode. The word firing is understood as meaning that a plasma that vaporizes or cuts the tissue forms on an electrode, here the active electrode.

In another exemplary embodiment, which embodiment in itself represents a refinement over the prior art even without a curved profile of the neutral electrode, the neutral electrode is produced in one piece with the neutral conductor from exactly one material or exactly one material mixture.

This embodiment may offer benefits from the point of view of production engineering. The neutral electrode and the neutral conductor are preferably formed from a continuous material and are not connected by shape-connecting measures such as pressing, soldering, welding, ultrasound treatment, etc. The neutral conductor is to be understood here as the conductor by which a potential required for the high-frequency current is routed from the proximal end of the instrument to the neutral electrode at the distal end of the instrument.

In another exemplary embodiment, which embodiment in itself represents a refinement over the prior art even without a curved profile of the neutral electrode, the neutral electrode, in relation to its transverse extent, extends less far in the distal direction in a central area than it does in side areas of the neutral electrode.

This embodiment makes it possible to improve a field of view of an optical device at the distal end of the instrument. While it is often the case in the prior art that the neutral electrode conceals an appreciable part of the field of view, this embodiment makes it possible to obtain an increased field of view by specifically reducing the size of the neutral electrode in some areas. Moreover, this embodiment can also serve the purpose of still further improved atraumatic handling.

In another exemplary embodiment, at least one portion of the neutral electrode extends in a plane that is at an angle to the longitudinal extent of the instrument.

This embodiment too permits an increased field of view. According to some exemplary embodiments, at least one curvature extends in this plane.

In another exemplary embodiment, which embodiment in itself represents a refinement over the prior art even without a curved profile of the neutral electrode, a distal limit of the neutral electrode is formed such that, between first and second areas of the neutral electrode that extend furthest in the distal direction, a third area is arranged which extends less far in the distal direction than the first and second areas.

This embodiment likewise serves the purpose of atraumatic handling of the instrument.

According to a second aspect, an electrosurgical system with a high-frequency generator and with an above-described instrument is made available, wherein the instrument can be attached to the high-frequency generator, and the high-frequency generator is able to provide an output power of at least 50 W according to some exemplary embodiments, at least 100 W according to other exemplary embodiments, at least 150 W according to yet other exemplary embodiments, and at least 200 W according to still other exemplary embodiments. In some embodiments of the electrosurgical system, the high-frequency generator is able to provide an output power of at least 350 W.

Further disclosure and features will become evident from the following description and from the attached drawing.

It will be appreciated that the features mentioned above and the features still to be explained below can be used not only in the respectively cited combination, but also in other combinations or singly, without departing from the scope of the present disclosure.

BRIEF DESCRIPTION OF THE DRAWINGS

Exemplary embodiments are depicted in the drawing and are explained in more detail in the description below. In the drawing:

FIG. 1 shows a side view of a bipolar medical instrument, here a resectoscope;

FIG. 2 shows a side view of elements inside the instrument according to FIG. 1;

FIG. 3 shows a plan view of elements inside the instrument according to FIG. 1;

FIG. 4 shows a perspective view of the elements according to FIG. 2;

FIG. 5 shows the enlarged detail A from FIG. 4;

FIG. 6 shows a slightly enlarged view of FIG. 2;

FIG. 7 shows the enlarged detail B from FIG. 6;

FIG. 10 shows the neutral electrode according to the above-described first embodiment;

FIG. 11 shows a neutral electrode according to a second embodiment;

FIG. 12 shows a neutral electrode according to a third embodiment;

FIG. 13 shows a neutral electrode according to a fourth embodiment;

FIG. 14 shows a neutral electrode according to a fifth embodiment;

FIG. 15 shows a neutral electrode according to a sixth embodiment;

DESCRIPTION OF EXEMPLARY EMBODIMENTS

Figure 8:
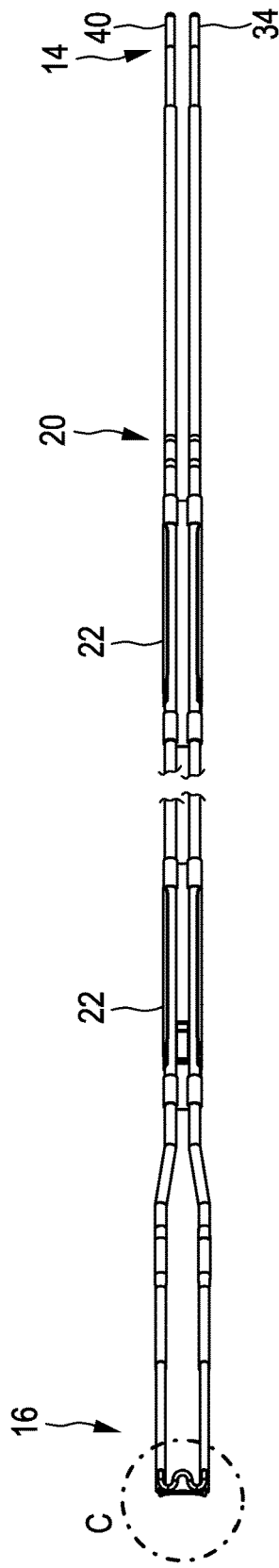
FIG. 8 shows a slightly enlarged view of FIG. 3.

FIG. 1 shows a side view of a bipolar medical instrument 10 for cutting tissue under the action of high-frequency current, here a resectoscope. The basic function of the instrument 10 is known from the prior art. In this connection, see in particular the patent specification EP 1 567 079 B1 (FIGS. 1-4, 6a and 6b; and paragraphs 47 to 72).

The instrument 10 extends along a longitudinal direction 12 from a proximal end 14 to a distal end 16. The instrument 10 is shown here in the retracted state. It will be seen that both the active electrode 30 (see FIG. 5) and also the neutral electrode 32 (see FIG. 5) are located inside a distal end of a shaft 18 of the instrument 10.

FIG. 2 is a side view showing an electrode carrier 20, which is arranged displaceably in the longitudinal direction 12 inside the shaft 18 and is guided by holding elements 22.

FIG. 3 shows a plan view of the electrode carrier 20 and of the holding elements 22. A transverse direction 24 is also indicated. Moreover, the figure indicates symbolically how the electrically active elements of the instrument 10 can be attached to a high-frequency generator 26, wherein the high-frequency generator 26 can here provide an output power of at least 200 W.

FIG. 4 shows a perspective view of the elements according to FIG. 2. At the distal end 16, part of the figure is identified by a circle and the letter A, which part is later shown enlarged.

FIG. 5 shows the enlargement of the detail A from FIG. 4. It will be seen that an active electrode 30 and a neutral electrode 32, adjacent to the active electrode 30, are arranged at the distal end 16. The active electrode 30 is designed as a wire loop.

The active conductor 34, here indicated by broken lines and connecting the active electrode 30 electrically to the high-frequency generator 26, is held in an insulating tube 36. On the other side, a conductor connected to the active electrode 30 is held in an insulating tube 38. Although the conductor can, like the active conductor 34, also be routed to the same pole of the high-frequency generator 26, it is sufficient if the conductor ends inside the tube 38, as is indicated here by the broken line. The conductor thus merely provides the active electrode 30 with a mechanical hold.

The neutral conductor 40, here indicated by broken lines and connecting the neutral electrode 32 electrically to the high-frequency generator 26, is held in an insulating tube 42. On the other side, a conductor connected to the neutral electrode 32 is held in an insulating tube 44. Although the conductor can, like the neutral conductor 40, also be routed to the same pole of the high-frequency generator 26, it is sufficient if the conductor ends inside the tube 44, as is indicated here by the broken line. The conductor thus merely provides the active electrode 30 with a mechanical hold.

It will be seen that the neutral electrode 32 has a curved profile with a first curvature 50 and second curvature 52, wherein the respective directions of the curvatures 50, 52 are different.

In the embodiment shown here, the curved profile additionally has a third curvature 54, and the directions of the curvatures change twice along the extension of the neutral electrode 32. The neutral electrode 32 is designed here as a wire element. A first surface of the active electrode 30 is smaller than a second surface of the neutral electrode 32.

In this embodiment, this may be achieved by the fact that the average cross section of the neutral electrode is larger, according to some exemplary embodiments, considerably larger, than the average cross section of the active electrode.

Here, a cross-sectional profile of the neutral electrode 32 has a rounded shape, which is here at least substantially circular. In view of the stated larger cross section, it can also be said here that the average diameter of the neutral electrode 32 is larger, according to some exemplary embodiments, considerably larger, than the average diameter of the active electrode 30.

In the embodiment shown here, the neutral electrode 32 is produced in one piece with the neutral conductor 40 from exactly one material or exactly one material mixture. Likewise, the active electrode 30 here is produced in one piece with the active conductor 34 from exactly one material or exactly one material mixture. According to some exemplary embodiments, active electrode 30 and active conductor 34, and also the neutral electrode 32 and the neutral conductor 40, are each formed together from a wire which leads from the proximal end of the electrode carrier 20 as far as the distal end 16 of the instrument 10.

FIG. 6 shows a slightly enlarged view of FIG. 2. At the distal end 16, part of the figure is identified by a circle and the letter B, which part is later shown enlarged.

FIG. 7 shows the enlargement of the detail B from FIG. 6. It will be seen that a portion of the neutral electrode 32, here the portion with the second curvature 52, extends in a plane 60 which is at an angle α to the longitudinal direction 12 of the instrument 10. The plane 60 is here perpendicular to the plane of the drawing and is therefore only indicated by a broken line. Relative to the longitudinal direction 12, a distal end 70 of the active electrode 30 is arranged at the same distal extent as a distal end 72 of the neutral electrode 32. In another embodiment (not shown), the distal end 70 of the active electrode 30 is arranged further distally than a distal end 72 of the neutral electrode 32. Relative to the orientation in the drawing, the active electrode 30 would in this case be arranged further to the left.

FIG. 8 shows a slightly enlarged view of FIG. 3. At the distal end 16, part of the figure is identified by a circle and the letter C, which part is later shown enlarged.

Figure 9:
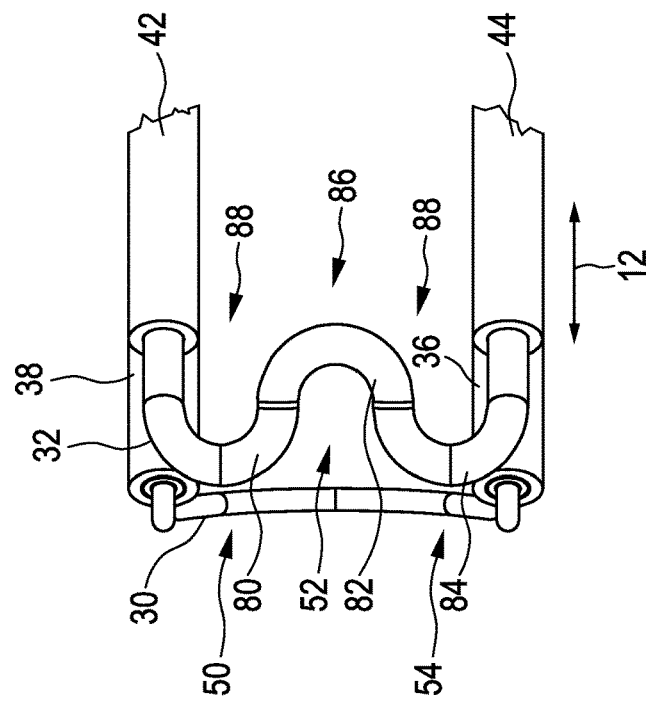
FIG. 9 shows the enlarged detail C from FIG. 8.

FIG. 9 shows the enlargement of the detail C from FIG. 8. In the plan view, the neutral electrode 32 has at least approximately a wave shape, here, at least approximately a W shape. The neutral electrode 32 has at least two curved portions, here three curved portions 80, 82, 84, which here in each case have at least approximately the shape of a semicircle or a half torus. The neutral electrode 32, in relation to its transverse extent along the transverse direction 24, extends less far in the distal direction in a central area 86 than it does in side areas 88.

FIG. 10 shows only the neutral electrode 32 in its insulating tubes 42, 44 according to the first embodiment described above. Relative to the orientation in the drawing, a distal limit of the neutral electrode 32 is here formed such that, between first and second areas 90, 92 of the neutral electrode 32 that extend furthest in the distal direction, a third area 94 is arranged which extends less far in the distal direction than the first and second areas 90, 92.

Further embodiments of the neutral electrode 32 are set out below. For the sake of clarity, not all of the reference signs are shown now, instead only certain selected reference signs that facilitate understanding. In principle, the explanations given in relation to the first embodiment apply to the subsequent embodiments, unless they are obviously not compatible with the specific embodiment.

FIG. 11 shows a neutral electrode 32 according to a second embodiment. The curved profile here has a total of five curvatures, of which the direction changes four times.

FIG. 12 shows a neutral electrode 32 according to a third embodiment. The embodiment shows that, even though a symmetry with respect to the central axis of the instrument 10 is chosen for some exemplary embodiments, such a symmetry is not absolutely necessary. According to some exemplary embodiments, the number of the curvatures and the radii of the curvatures can be chosen at the discretion of a person skilled in the art.

FIG. 13 shows a neutral electrode 32 according to a fourth embodiment. It will be seen that it is not only circular curvatures that can be chosen, but also rounded forms of another type. The radii of the curvatures can in principle be chosen to be very small, provided that the distal end of the neutral electrode 32 does not form a tip that can cause trauma.

FIG. 14 shows a neutral electrode 32 according to a fifth embodiment. Here, the second curvature 52 or third area 94 is designed with an enlarged diameter.

FIG. 15 shows a neutral electrode 32 according to a sixth embodiment. Here, the first and third curvatures 50, 54 or the first and second areas 90, 92 are designed with an enlarged diameter.

Figure 16:
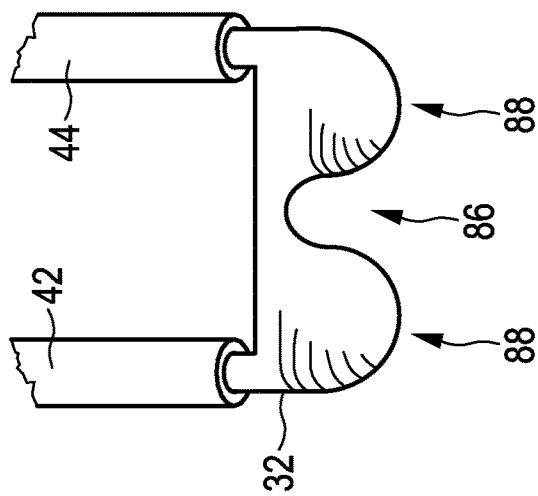
FIG. 16 shows a neutral electrode according to a seventh embodiment.

FIG. 16 shows a neutral electrode 32 according to a seventh embodiment. At its distal limit, the seventh embodiment corresponds to the first embodiment (see FIG. 10). It will be seen that the neutral electrode 32 does not have to be designed as a wire and instead can also be designed flat.

Figure 17:
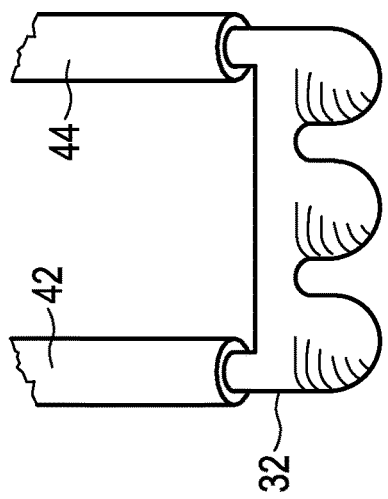
FIG. 17 shows a neutral electrode according to an eighth embodiment.

FIG. 17 shows a neutral electrode 32 according to an eighth embodiment. At its distal limit, the eighth embodiment corresponds to the second embodiment (see FIG. 11). It will be seen that the neutral electrode 32 does not have to be designed as a wire and instead can also be designed flat.

Figure 18:
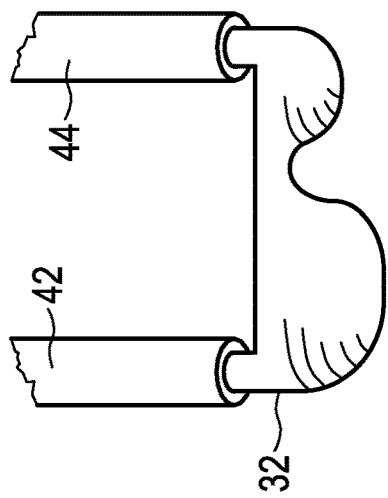
FIG. 18 shows a neutral electrode according to a ninth embodiment.

FIG. 18 shows a neutral electrode 32 according to a ninth embodiment. At its distal end, the ninth embodiment corresponds to the third embodiment (see FIG. 12). It will be seen that the neutral electrode 32 does not have to be designed as a wire and instead can also be designed flat.

Thus, a bipolar medical instrument has been disclosed with which it may be possible to work in a particularly atraumatic manner and which may offer advantages during production.

The invention claimed is:

1. A bipolar medical instrument for cutting tissue under the action of high-frequency current, wherein the instrument extends along a longitudinal direction from a proximal end to a distal end, and
    wherein an active electrode and a neutral electrode, adjacent to the active electrode, are arranged at the distal end, wherein the neutral electrode has a curved profile with a first curvature and a second curvature, the respective directions of the first and second curvatures being different, wherein the neutral electrode, when viewed from a top plan view, is at least approximately W-shaped, and wherein the neutral electrode extends in a transverse direction perpendicular to the longitudinal direction such that a width of the neutral electrode in the transverse direction substantially matches a width of the instrument at the distal end.

2. The instrument of claim 1, wherein the curved profile additionally has a third curvature, and the directions of the first, second, and third curvatures change twice along the extension of the neutral electrode.

3. The instrument of claim 1, wherein the neutral electrode is configured as a wire element.

4. The instrument of claim 1, wherein a first surface of the active electrode is smaller than a second surface of the neutral electrode.

5. The instrument of claim 1, wherein a cross-sectional profile of the neutral electrode has at least one of a rounded shape, an oval shape, or a circular shape.

6. The instrument of claim 1, wherein the neutral electrode has a constant cross section along a physical extension of the neutral electrode.

7. The instrument of claim 1, wherein the neutral electrode has a constant diameter along a physical extension of the neutral electrode.

8. The instrument of claim 1, wherein the neutral electrode has at least three curved portions.

9. The instrument of claim 8, wherein each curved portion has at least approximately the shape of a partial oval or a partial circle.

10. The instrument of claim 1, wherein the active electrode and the neutral electrode, when in a retracted state, are located inside a distal end of a shaft of the instrument.

11. The instrument of claim 1, wherein a distal end of the active electrode is arranged further distally in the longitudinal direction than a distal end of the neutral electrode.

12. The instrument of claim 1, wherein a distal end of the active electrode and a distal end of the neutral electrode are arranged at a same distal extent in the longitudinal direction.

13. The instrument of claim 1, wherein the neutral electrode is produced in one piece with a neutral conductor from exactly one of a material or a material mixture.

14. The instrument of claim 1, wherein the neutral electrode, in relation to the transverse extent, extends less far in a distal direction in a central area than it does in side areas of the neutral electrode.

15. The instrument of claim 1, wherein at least one portion of the neutral electrode extends in a plane that is at an angle to a longitudinal extent of the instrument.

16. The instrument of claim 1, wherein a distal limit of the neutral electrode is formed such that, between first and second areas of the neutral electrode that extend furthest in a distal direction, a third area is arranged which extends less far in the distal direction than the first and second areas.

17. An electrosurgical system comprising a high-frequency generator, and the instrument of claim 1 which can be attached to the high-frequency generator.

18. A medical instrument for cutting tissue, comprising:
a shaft extending in a longitudinal direction from a proximal end to a distal end;
an electrode carrier disposed in the shaft and displaceable in the longitudinal direction;
an active electrode disposed on a distal end of the electrode carrier;
a neutral electrode disposed on the distal end of the electrode carrier and adjacent to the active electrode; and
the neutral electrode has a first curved portion, a second curved portion, and a third curved portion disposed between the first curved portion and the second curved portion, the first curved portion and the second curved portion having the same direction of curvature, the third curved portion having a direction of curvature different from the first and second curved portions, wherein the first curved portion and the second curved portion are positioned further in a distal direction than the third curved portion.

19. A medical instrument for cutting tissue, comprising:
a shaft extending in a longitudinal direction from a proximal end to a distal end;
an electrode carrier disposed in the shaft and displaceable in the longitudinal direction;
an active electrode disposed on a distal end of the electrode carrier;
a neutral electrode disposed on the distal end of the electrode carrier and adjacent to the active electrode;
wherein the neutral electrode has two ends connected to the electrode carrier and a middle section between the two ends, the middle section being inclined at an acute angle relative to the two ends.

* * * * *